US006881959B2

(12) United States Patent
Meng et al.

(10) Patent No.: US 6,881,959 B2
(45) Date of Patent: Apr. 19, 2005

(54) METHOD AND SYSTEM FOR GENERATING AN IMAGE OF THE RADIATION DENSITY OF A SOURCE OF PHOTONS LOCATED IN AN OBJECT

(75) Inventors: Ling Jian Meng, Ann Arbor, MI (US); Neal H. Clinthorne, Ann Arbor, MI (US); W. Leslie Rogers, Ann Arbor, MI (US); David K. Wehe, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 273 days.

(21) Appl. No.: 10/285,211

(22) Filed: Oct. 31, 2002

(65) Prior Publication Data

US 2004/0084624 A1 May 6, 2004

(51) Int. Cl.[7] ................................................. G01T 1/20
(52) U.S. Cl. ................ 250/363.1; 250/366; 250/370.09
(58) Field of Search ............................. 250/363.1, 366, 250/367, 370.01, 370.09, 370.1

(56) References Cited

U.S. PATENT DOCUMENTS

| | | | | |
|---|---|---|---|---|
| 4,506,374 | A | | 3/1985 | Flynn |
| 4,529,882 | A | * | 7/1985 | Lee .......................... 250/363.1 |
| 5,462,056 | A | | 10/1995 | Hawman et al. |
| 5,506,408 | A | * | 4/1996 | Vickers et al. .............. 250/366 |
| 6,175,116 | B1 | * | 1/2001 | Gagnon et al. ......... 250/363.03 |
| 6,323,492 | B1 | | 11/2001 | Clinthorne |
| 6,359,279 | B1 | | 3/2002 | Gagnon et al. |
| 6,448,560 | B1 | * | 9/2002 | Tumer .................... 250/370.09 |
| 6,484,051 | B1 | * | 11/2002 | Daniel ......................... 600/436 |
| 6,737,652 | B1 | * | 5/2004 | Lanza et al. ........... 250/363.06 |
| 6,791,090 | B1 | * | 9/2004 | Lin et al. ..................... 250/367 |

OTHER PUBLICATIONS

Wilson, D.W., et al., Reconstruction of Two–and Three–Dimensional Images From Synthetic–Collimator Data, IEE Transactions on Medical Imaging, vol. 19, No. 5, May 2000.

Uritani, A., et al. in Electronically–Collimated Gamma Camera with a Parallel Plate Collimator for Tc–99m Imaging, IEEE Trans. Nucl. Sci., vol. 44, pp. 894–898, 1997.

Smith, L.E., et al., Hybrid Collimation for Industrial Gamma–Ray Imaging: Combining Spatially Coded and Compton Aperture Data, Nucl. Instr. Meth., A462, pp. 576–587, 2001.

Leblanc, J.W., et al., C–SPRINT: A Prototype Compton Camera System for Low Energy Gamma Ray Imaging, IEEE Trans. Nucl. Sci., vol. 45, pp. 943–949, 1998.

Meikle, S.R., An Investigation of Coded Aperture Imaging for Small Animal SPECT, IEEE Trans. Nucl. Sci., vol. 48, pp. 816–821, 2001.

Singh, M., et al, An Electronically Collimated Gamma Camera for Single Photon Emission Computed Tomography, Part I: Theoretical Consideration and Design Criteria, Med. Phys., vol. 10, pp. 421–427, 1983.

* cited by examiner

*Primary Examiner*—Albert Gaglairdi
(74) *Attorney, Agent, or Firm*—Brooks Kushman P.C.

(57) ABSTRACT

Method and system for generating an image of the radiation density of a source of photons located in an object wherein Compton scattering and non-Compton scattering events are detected and contained within data used for image reconstruction. The system includes a multiple pinhole collimator, a position sensitive scintillation detector as used in standard Gamma cameras, and a silicon pad detector array inserted between the collimator and the scintillation detector. The problem of multiplexing, normally associated with multiple pinhole systems, is reduced by using the extra information from the detected Compton scattering events. For properly selected pinhole spacing, this leads to a significantly improved image quality. A valuable enhancement can be achieved when adding only a small fraction of gamma rays with reduced angular ambiguity. The system does not require a highly optimized Compton camera behind the collimator.

16 Claims, 3 Drawing Sheets

METHOD AND SYSTEM FOR GENERATING AN IMAGE OF THE RADIATION DENSITY OF A SOURCE OF PHOTONS LOCATED IN AN OBJECT

STATEMENT REGARDING FEDERALLY SPONSORED RESEARCH OR DEVELOPMENT

This invention was made with government support under NIH Grant No. CA 32846. The Government has certain rights in the invention.

BACKGROUND OF THE INVENTION

1. Field of the Invention

This invention relates to methods and systems for generating an image of the radiation density of a source of photons located in an object.

2. Background Art

Parallel hole and pinhole are by far the most often used collimation methods for nuclear medicine applications, although fanbeam and conebeam collimators are also applied. These collimators have the advantage of being non-multiplexing and therefore every detected gamma ray defines a unique compact angular region, within which the gamma ray was generated or scattered. However, this uniqueness of information is achieved at the price of throwing away all other photons that do not fall into those possible paths defined by the collimator. Despite their drawback in sensitivity, these collimation methods are widely used in commercially available Gamma cameras.

Several mechanical collimators involving certain degrees of multiplexing have been studied in the past. These include the use of coded apertures, multiple pinholes and rotating slits, which allows a better detection sensitivity to be achieved. Unfortunately, this improvement is usually achieved at the expense of the amount of information conveyed by each detected photon. As a result, the signal-to-noise ratio in the collected data deteriorates dramatically when continuous background is introduced. In order to decode the data to provide a useful image, an unrealistically large number of counts are normally required. The uses of these image formation methods are currently limited to some particular imaging applications, in which the object-to-background ratio is reasonably large.

This trade-off is the same for Compton cameras. The information carried by the detected photons is diluted into a conical surface rather than a single ray. Furthermore, the angular accuracy achievable is also limited by the effect of Doppler broadening and electronic noise, especially at lower energies. It has been shown that at 140 keV, to compete with conventional gamma cameras the design of a Compton camera may require an unrealistic amount of semiconductor material for the scattering detector to provide enough detected scattering events.

In order to improve the imaging quality of multiplexing imaging systems, Wilson et al. proposed a so-called "synthetic collimator" in "A High Resolution Synthetic Collimator," JOURNAL OF NUCLEAR MEDICINE, Vol. 39, p. 361, 1998. It is similar to a conventional multiple pinhole system, except the multiple pinhole aperture is moved between the object and detector during the data collection. As a result, data with different degrees of multiplexing is collected. It improves the condition number of the system response function to be inverted in the image reconstruction stage. It is shown that such an arrangement offers a superior reconstruction resolution when compared to a similar detector with a parallel hole collimator. The use of "synthetic collimation" also permits some three-dimensional information to be extracted. However, such a detector concept requires a detector with very good spatial resolution. The advantages of a "synthetic collimator" are also reduced dramatically when statistical noise is present in the data.

The idea of using combined mechanical and electronic collimation was proposed by Uritani et al. in "Electronically-Collimated Gamma Camera with a Parallel Plate Collimator for Tc-99 m Imaging," IEEE TRANS. NUCL. SCI., Vol. 44, pp. 894–898, 1997. It reduces the effect of multiplexing while maintaining a relatively high open fraction on the collimator. In their detector, a multiple parallel plate collimator was placed in front of a Compton camera. The results showed an improved signal-to-noise ratio for imaging $^{99m}$Tc tracer. However, the raw detection sensitivity is limited by the relatively low probability of detecting photons through Compton scattering effect.

Smith et al. have also reported a detector design with a similar concept in "Hybrid Collimation for Industrial Gamma-Ray Imaging: Combining Spatially Coded and Compton Aperture Data," NUCL. INSTR. METH., A462, pp. 576–587, 2001. The design uses a coded aperture collimator in front of a Compton camera.

Other related articles include: J. W. LeBlanc et al., "C-SPRINT: A Prototype Compton Camera System for Low Energy Gamma Ray Imaging," IEEE TRANS. NUCL. SCI., Vol. 45, pp. 943–949, 1998; S. R. Meikle et al., "An Investigation of Coded Aperture Imaging for Small Animal SPECT," IEEE TRANS. NUCL. SCI., Vol. 48, pp. 816–821, 2001; and M. Singh et al., "An Electronically Collimated Gamma Camera for Single Photon Emission Computed Tomography, Part I: Theoretical Consideration and Design Criteria," MED. PHYS., Vol. 10, pp. 421–427, 1983.

Related U.S. patents include: U.S. Pat. Nos. 4,506,374; 4,529,882; 5,462,056; 6,323,492; and 6,359,279.

SUMMARY OF THE INVENTION

An object of the present invention is to provide a practical and cost-effective method and system for generating an image of the radiation density of a source of photons located in an object in real-time to improve image quality by utilizing extra information from detected Compton scattering events.

In carrying out the above object and other objects of the present invention, a method for generating an image of the radiation density of a source of photons located in an object is provided. The method includes mechanically collimating photon emissions from the object to obtain mechanically-collimated photon emissions. The method also includes detecting Compton and non-Compton scattering events. An image is reconstructed from data containing detected Compton scattering events and detected non-Compton scattering events.

The step of mechanically collimating may include the step of sampling the object at several view angles substantially simultaneously.

Further in carrying out the above object and other objects of the present invention, a system for generating an image of the radiation density of a source of photons located in an object is provided. The system includes a mechanical collimator to mechanically collimate photon emissions from the object to obtain mechanically-collimated photon emissions. Detectors detect Compton and non-Compton scattering events. A processor reconstructs an image using data containing detected Compton scattering events and detected non-Compton scattering events.

The detectors may include a scintillation detector and a scattering detector provided between the mechanical collimator and the scintillation detector.

The scintillation detector may be position-sensitive.

The scattering detector may be a detector array such as a silicon pad detector array.

The mechanical collimator may include a multiple-pinhole collimator and a different probability may be assigned for each pinhole.

The probability assigned each pinhole may be based upon:

(1) in the case of non-Compton scattering events, position recorded in the scintillation detector; and (2) in the case of Compton scattering events, positions and energies recorded in the detectors.

The mechanical collimator may include a multiple-pinhole collimator and the object may be sampled at several view angles substantially simultaneously.

The mechanical collimator may be spatially or temporally modulated and may be designed to have a favorable cross-correlation pattern with the Compton detector.

The detectors may include an Anger camera.

The detectors may include a scattering detector.

The photon emissions may be gamma emissions.

The above object and other objects, features, and advantages of the present invention are readily apparent from the following detailed description of the best mode for carrying out the invention when taken in connection with the accompanying drawings.

DETAILED DESCRIPTION OF THE PREFERRED EMBODIMENTS

In general, the present invention combines mechanical collimation provided by a coded aperture, a multiple pinhole or a rotating slit with electronic collimation provided by a Compton scattering camera. It offers improved detection sensitivity and imaging capability compared with a standard Gamma camera using parallel hole or pinhole collimation. A multiple pinhole, a rotating slit collimator or a coded aperture is combined with electronic collimation in such a way that the low spatial frequency signal detected using the Compton camera is combined, in real-time, with the high spatial frequency components provided by the mechanical collimation. This information is used in image reconstruction, and offers a superior image quality comparing with using solely one collimation method.

Figure 1:
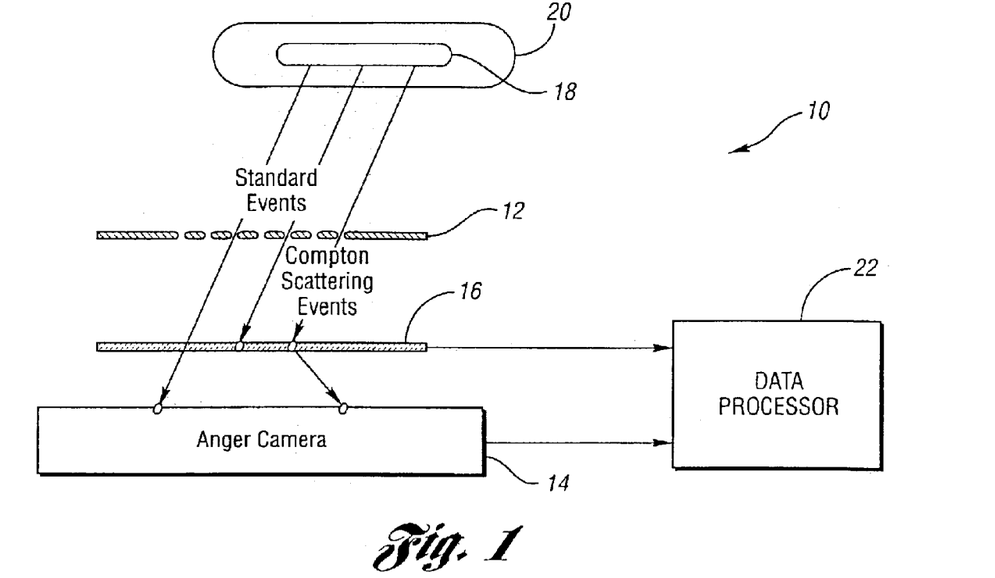
FIG. 1 is a schematic diagram of the Compton scattering enhanced multiple pinhole imaging system of the present invention.

Referring now to FIG. 1, a system of the invention, generally indicated at 10, includes a mechanical collimator, such as a multiple-pinhole collimator 12, a position sensitive scintillation detector (within Anger camera 14) as used in a standard Gamma camera, and a position sensitive semiconductor detector array (i.e., scattering detector) 16, inserted between the collimator 12 and the scintillation detector. The detector array 16 is used as the scattering detector to scatter the incoming gamma rays. A proportion of these scattered gamma rays are then stopped in the Anger camera 14. These events provide some extra angular information based on a broadened conical surface defined by the energy deposited in the scattering detector 16 and the interaction positions in both the scattering and secondary detectors 16 and 14, respectively. FIG. 1 also shows a source 18 of photons located within an object 20.

The problem of multiplexing, normally associated with multiple pinhole systems, is reduced through the use of the information provided by the Compton scattering events, detected in the scattering detector 16 and the scintillation detector 14 and processed in a data processor 22.

The choice of using the multiple pinhole collimator 12 offers a wide range of freedom in selecting the open fraction of the collimator 12 and spatial coding scheme for different applications. To overcome the problem of low sensitivity, the system 10 is designed to collect events both Compton scattered between the two detectors and interact with either the first or the second detector only. Therefore, the raw sensitivity is not limited by the Compton aperture. The combined data is then used in a list-mode reconstruction performed in the data processor 22.

The system 10 is essentially the combination of a Gamma camera using the multiple pinhole collimator 12 and the silicon scattering detector 16 inserted between the Anger camera 14 and the collimator 12, as shown in FIG. 1. The extra information from Compton scattering not only enables one to say that the detected photon is from one of the pinholes in the aperture, but also assigns different probability for each pinhole. The system 10 also makes use of those events that interact with either the first or the second detector only. The combined data set containing both Compton scattered and Non-Compton scattered events is used in list-mode image reconstruction algorithms performed in the processor 22. Since the Compton aperture is not designed for imaging by itself, but rather for restricting the already restricted angular uncertainty (through the mechanical aperture). It is possible to use a less optimized Compton camera while still providing useful extra information. The configuration shown in FIG. 1 is an optimized one. What follows now is a demonstration of the performance benefit of adding the Compton aperture to a mechanically collimated system.

A Simple 2-D Case

The performance benefit is first demonstrated by a simple 2-D imaging case. In this study, an idealized position sensitive detector with 128×128 2×2 mm pixels was simulated. It is assumed to have infinite stopping power and zero readout noise. A multiple pinhole collimator was placed 8 cm away from the detector. It has seven 2 mm diameter pinholes in a hexagonal pattern with 1.5 cm spacing. No aperture penetration was allowed in the simulation. A 12×12 $cm^2$, 2-D object was placed 8 cm away from the collimator. The data is generated so that one can control the percentage of events, for which one knows exactly which pinhole the photon is coming from. In this study, these events are called "extra information" (EI) and several data sets were generated with this percentage ranging from 0 to 100%. For each percentage of EI, 100 realizations were generated. The image reconstruction was performed using standard MLEM algorithm. The FWHM of Local Impulse Response (LIR) was used as an indication of the achieved spatial resolution. The number of iterations is so chosen that all reconstructions result in the same spatial resolution. The LIR was derived by adding a small disturbance to a pixel in the source-object and subtracting the images reconstructed using mean projections with and without this disturbance. The reason for setting up such as simple test is to get an indication of the improvement in image quality as a function of the amount of extra information added. This is relatively difficult to evaluate when a realistic Compton aperture configuration is used.

Reconstructions in 3-D

Figure 2:
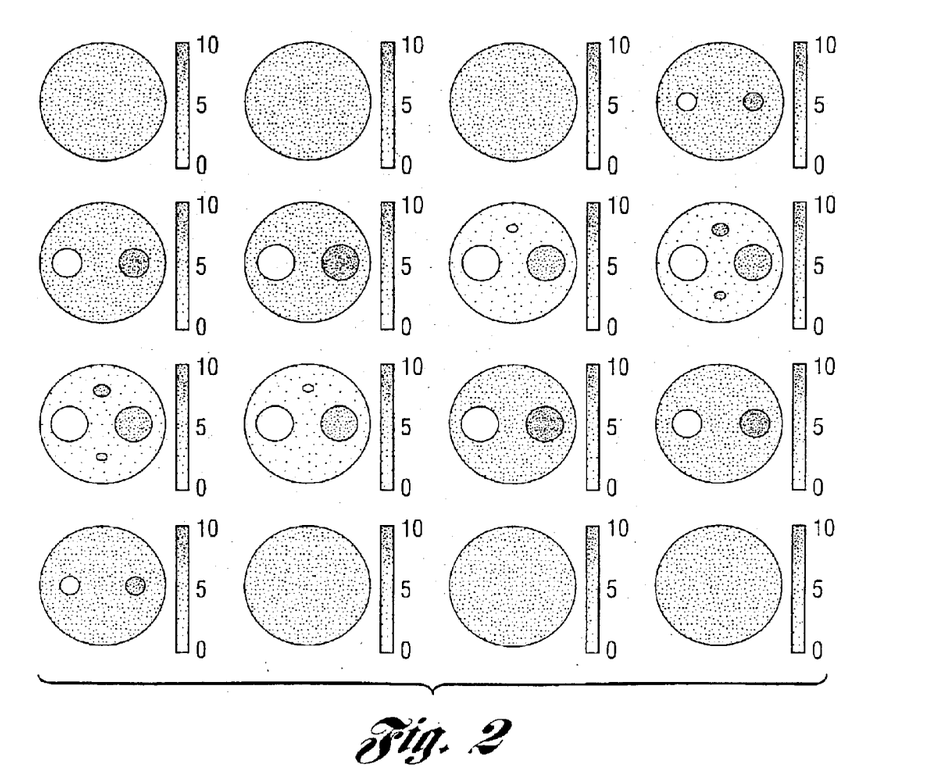
FIG. 2 is an activity distribution of a simulated objected used in a 3-D study.

In this study, the performance benefits were evaluated based on a more realistic detector configuration and a 3-D object. The detector system used consists of a silicon first detector, a NaI/PMT Anger camera and a multiple pinhole collimator. The first pinhole collimator studied has 25 pinholes placed on a 5×5 square grid with 2 cm spacing. In order to reduce the possible artifacts from sampling the object at several discrete spatial frequencies, the actual location of pinholes are randomized around each grid point for around 2 mm. A second collimator was also studied with 49 pinholes in a 7×7 square grid and a reduced pinhole distance. Two such detectors were placed above and below the object. The object simulated is assigned an activity distribution as shown in FIG. 2. It contains four hot or cold spheres, immersed in a continuous background. Details of the detector and source geometry are summarized in Table 1.

quality achievable with the detector as a function of the bias. Barrett et al. proposed to use the linear discrimination of a known signal against a known background as a figure-of-merit. This approach is widely used in observer performance studies. However, most of the current studies are based on some very simple and somehow unrealistic imaging tasks, such as the Signal-Known-Exactly and Background-Known-Exactly case. It has been shown that the simplicity of this task limits its use in optimizing system design. In recent years, many efforts have been made in trying to set up a more realistic imaging task for the observer studies and this remains a very active area. Hero and Fessler proposed to use the Uniform Cramer-Rao bound (Uniform CR bound) to study the variance-bias trade-off of an estimator. It gives the lowest possible variance at a certain bias described by the bias gradient norm. (It is in turn closely related to the Local Impulse Response.) This method, however, requires inversion of Fisher Information Matrix (FIM) and therefore requires a huge memory load and computation. Moreover, for some imaging cases in which the size of the FIM itself is too big to be fully calculated and fitted into memory, the inversion becomes more difficult.

Fessler and Rogers have proposed an approach that analyzes the mean, variance and spatial resolution properties of images estimated through optimizing an implicitly defined object function, such as the Penalized Likelihood or Maximum a priori (MAP) estimators. This method was also used in developing a pre-conditioner for Conjugate Gradient PET image reconstruction. Qi et al. further explored this idea by adapting this pre-conditioner as an approximation of the

TABLE 1

PARAMETERS USED IN THE SIMULATION

|  | First Detector | Second Detector | Multiple Pinhole Aperture | Object |
| --- | --- | --- | --- | --- |
| Total Size (mm) | 250 × 250 × 7.5 | 400 × 400 × 6 | 250 × 250 × 5 | 96 × 96 × 48 |
| Pixel Size (mm) | 2.5 × 2.5 × 2.5 mm | 4 × 4 × 6 | (Pinhole size) ø1.5 mm | 3 × 3 × 3 |
| No. of Pixels | 100 × 100 × 3 (3 × $10^4$) | $10^4$ | (No. of pinholes) 25 or 49 | 16 × 32 × 32 (16384) |
| Z-location (mm) | −50 | −150 | 0 | 50~100 |
| Material | Si | NaI(Tl) | Tungsten | Air |
| Energy Resolution | 1 keV | 10% at 140 keV | — | — |
| Energy Threshold | 10 keV | 20 keV | — | — |
| Notes | 1. Doppler Broadening is included | 1. Depth of interaction not included. 2. Resolution is equal to pixel size. | 1. Aperture penetration is modeled. 2. Photons scattered in collimator ignored. | 1. Object scattering and attenuation ignored. |

Due to the large number of detector bins and source voxels involved, it is impractical to precalculate and store the entire system response function (SRF). Instead, several sub-SRFs corresponding to factors such as collimator transfer function were precalculated and stored, Compton scattering at every possible angle and the probability of detection after scattering, etc. The data was generated in list-mode and SRF corresponding to a particular realization was precomputed and stored in memory. This pre-computation is the most time-consuming step. It limits the total number of counts that can be reconstructed to one million. The images were reconstructed in 3-D using the list-mode MLEM algorithm.

Variance-Resolution Trade-Off

In nuclear medicine, it is a normal practice that the reconstructed image is a biased estimate of the true object, in the presence of statistical noise and imperfections in the system model. This is true for the popular MLEM, Maximum a priori (MAP) algorithms and analytical reconstruction methods such as filtered back-projection. It is, therefore, important to compare the detector performance or the image Hessian matrix and developing a closed form approximation for resolution and variance. This later development utilized the Fourier Transform theory with or under the assumption that the systems modeled are "locally shift-invariant." It has been shown that although several approximations have been used in reaching the closed form expressions of variance and resolution, the results had very good agreement with Monte Carlo simulations. These expressions also provide some very useful insight into the final solution achieved using MAP reconstruction algorithms. Another important feature is that this approach does not require the inversion of the Hessian matrix. Therefore, the computation load is greatly reduced, especially when only the image property at a few pixels is required.

One could argue that the spatial resolution and variance property derived using this approach is only based on a particular reconstruction algorithm. There is no guarantee that these results can be generalized to situations in which different reconstruction methods are used. The arguments one would use to support this choice are the following. Theoretically, it has been shown that the Uniform CR bound on the variance of estimators with a certain bias-gradient can actually be achieved by MAP reconstruction with the appropriate prior.

The details of the development leading to this method can be found in the prior art. Some of the key steps and the final results are briefly restated. Given a measured data set y, the log-likelihood of an estimator x, of the underlying object is:

$$L(Y|X) = \Sigma y_i \log \bar{y}_i - \bar{y}_i \qquad (1)$$

where $X \in R^n$ is the image and $Y \in R^m$ is the measured data. The mean of the data is related to the image X through transformation:

$$\bar{y} = Px + r \qquad (2)$$

where P is the detector response function and r is the mean contribution from object scattering events and background radiation. The matrix P is the system response function to the incoming gamma rays. It takes into account both the probability of detecting a Compton scattering event and the probability of detecting a non-Compton scattering event, given a gamma ray is generated in the source object. In MAP reconstruction, the solution achieved is also influenced by our a priori information about the object, represented by function R(x). In order to control the amount of this influence, a Lagrange multiplier is introduced, which results in an object function:

$$\Phi(x, y) = L(y|x) + \beta R(x) \qquad (3)$$

In this study, only the quadratic roughness penalty was used with the form:

$$R(x) = \sum_j \frac{1}{2} \sum_i w_{ij} \phi(x_j - x_i) \qquad (4)$$

where $w_{ij}$ is the weighting factor that takes into account the 26 neighbors and $$\phi(t) = t^2 \qquad (5)$$

The MAP estimator can be achieved by maximizing this objective function:

$$\hat{x} = \arg\max_x \Phi(x, y) \qquad (6)$$

For a non-linear estimator, one can use the local impulse response (LIR) as a measure of the spatial resolution property. For the jth voxel it is defined as:

$$l^j(\hat{x}) = \lim_{\delta \to 0} \frac{E(y(x+\delta e_j)) - E(y(x))}{\delta} = \frac{\partial}{\partial x_j} \hat{x}(y(x)) \qquad (7)$$

Using the first order Taylor expansion and chain rule, one can approximate the local impulse response by its linearized representation:

$$l^j \approx \frac{\partial}{\partial x_j} \hat{x}(y(x)) \approx [F + \beta R(\hat{x})]^{-1} F e_j \qquad (8)$$

where $F = P'D[1/\bar{y}_i]P$ is the Fisher information matrix. One can similarly show that the covariance of MAP reconstruction can be approximated as:

$$Cov(\hat{x}) \approx [F+\beta R]^{-1} F [F+\beta R]^{-1} \qquad (9)$$

One can calculate the local impulse response function and variance at a certain point through calculating a row of the inversed matrix $[F+\beta R]$.

Although this method is independent of the particular optimizing algorithm and agrees well with the Monte Carlo results, the computation cost remains high. It involves inversion of Hessian matrix or solving related linear equations. For the detector geometry proposed, the number of detector bins is on the order of $10^9$. If 16384 source pixels are involved, calculating the Fisher Information Matrix becomes a challenging task. To make the calculation computationally practical, one needs to make further simplification. Here, the approximations proposed by Fessler et al. are adopted in developing a pre-conditioner for conjugate gradient specifically, the pre-conditioner itself was used as the approximation of the Hessian matrix to be inverted. The key approximation leading to this development is bringing the diagonal matrix sandwiched between P' and P outside so that:

$$F = P'D[1/\bar{y}_i]P \approx D_k P'PD_k \qquad (10)$$

and similarly $$\beta R(\hat{x}) = \beta D_k D_\eta C'C D_\eta D_k \qquad (11)$$

where $D_k = D[K_j]$ with $$K_j = \sqrt{\frac{\sum_i P_{ij}^2 / \bar{y}_i}{\sum_i P_{ij}^2}} \qquad (12)$$

and $D\eta = D[\eta_j]$ with $$\eta_j = \sqrt{\frac{\beta}{k_j} \frac{\sum_k c_{kj}^2 \ddot{\phi}([C\hat{x} - m])}{\sum_i c_{kj}^2}} \qquad (13)$$

where $\ddot{\phi}(t) = d^2/dt^2 \phi(t)$. Substituting (7) and (8) into (5), one gets the approximation for the local impulse response $$l^j \approx [P'P + \eta_j^{-2} C'C]^{-1} P'P e_j \qquad (14)$$

For a shift-invariant system, the matrix P'P and C'C have block-toeplitz structure and therefore can be approximated by their block-circulate forms. The eigenvectors, $\lambda_i$ and $\mu_i$, of the block-circulate representations of P'P and C'C can be easily derived using the 3-D Fourier transform. This property was used by Qi to develop a closed form expression of the local impulse response and variance of MAP reconstruction as follows:

$$l^j(\hat{x}) = Q'D\left[\frac{\lambda_i}{\lambda_i + \eta_j^2(\hat{x})\mu_i}\right] Q e_j \qquad (15)$$

$$Var_j(\hat{x}) \approx \frac{k_j^{-2}}{N} \sum_i \frac{\lambda_i}{(\lambda_i + \eta_j^2(\hat{x})\mu_i)^2} \qquad (16)$$

where Q and Q' are the unitary 3-D discrete Fourier transform operator and its transpose.

There are several issues worth noting about this approach. First, these approximations are originally developed for 2-D PET case, in which the detector response function can be assumed to be shift-invariant. This is, however, certainly not valid for the system 10. To proceed, one needs to make further approximation that the system is, at least, "locally shift-invariant." The key of this approximation lies in the assumption that the imaging property of a voxel j is largely determined by the group of voxels around it, for which the detector's response to these voxels are linearly correlated to that of the target voxel (which results in a non-zero entry in the jth column of the FIM). When studying the resolution and variance of a voxel, other columns of the FIM can be approximated by the shifted version of this column. Secondly, in the implementation of this method, the eigenvalues of the matrix P'P are derived by 3-D Discrete Fourier Transform of the jth column of the matrix. This requires that P'P has a block-Toeplitz structure and therefore the actual column can be replaced by its block-circulate approximation. Although this approximation is fairly accurate in situations, such as optical image deblurring, and produces satisfactory accurate results in the context of 3-D PET, its applicability in limited angle tomography has not been evaluated. In order to utilize equations (15) and (16), one needs to symmetrize the jth column of the FIM and truncate the negative FFT coefficients after FFT to make sure that the approximated FIM is non-negative definite. This, in fact, modifies the column of P'P, so that the non-zero entries become more concentrated in the vicinity of the pixel of interest. (This effect can be seen by inverse FFT of the truncated Fourier coefficients.) The effect of this modification is certainly dependent on the particular detector configuration used. In order to verify the accuracy of this approach in predicting the performance of the proposed detector, a limited Monte Carlo simulation was carried out to provide a few data points.

Results in the Simple 2-D Case

Figure 3:
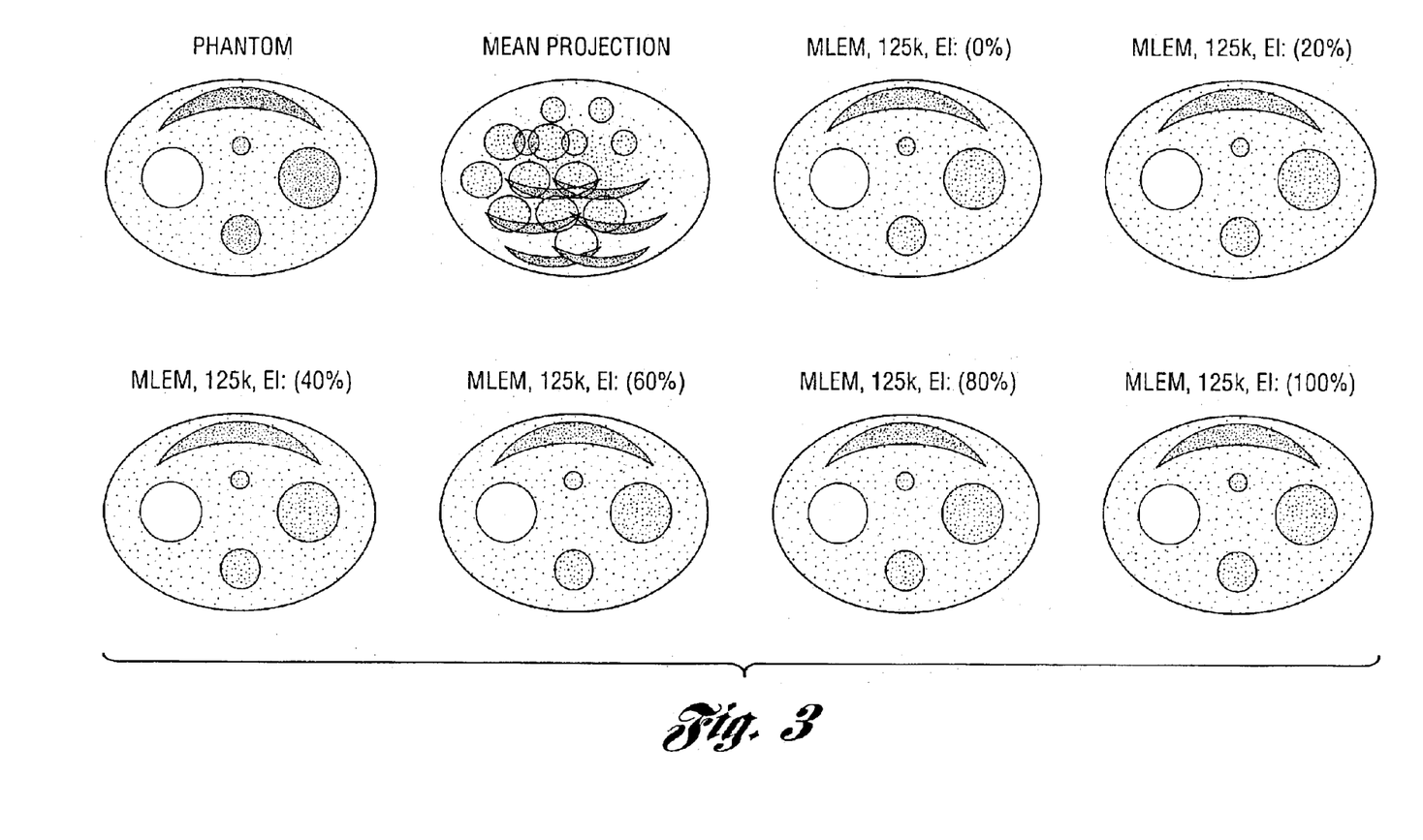
FIG. 3 shows reconstructed images based on data sets containing 125K events including simulated phantom, mean projection and the reconstructed images with different percentages of extra information (EI) included in the reconstruction; an EI of x % indicates that within all events used, there are x % events for which the pinhole it came from is known exactly.
Figure 4A:
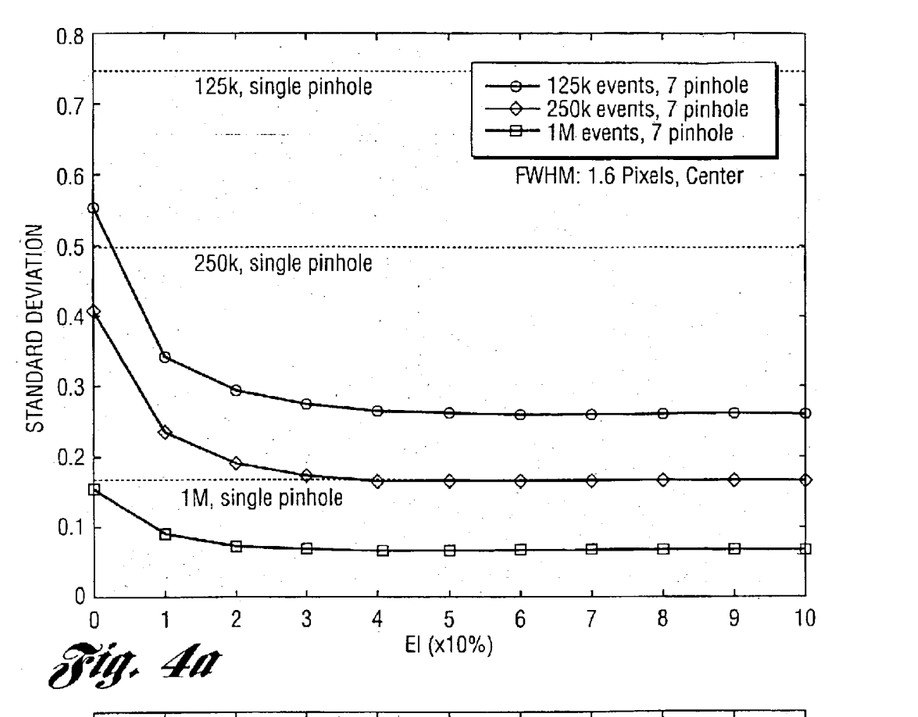
FIGS. 4a and 4b are graphs wherein the graphs of FIG. 4a show standard deviation of a center pixel and FIG. 4b shows standard deviation of an edge pixel, all of which are a function of added EI.
Figure 4B:
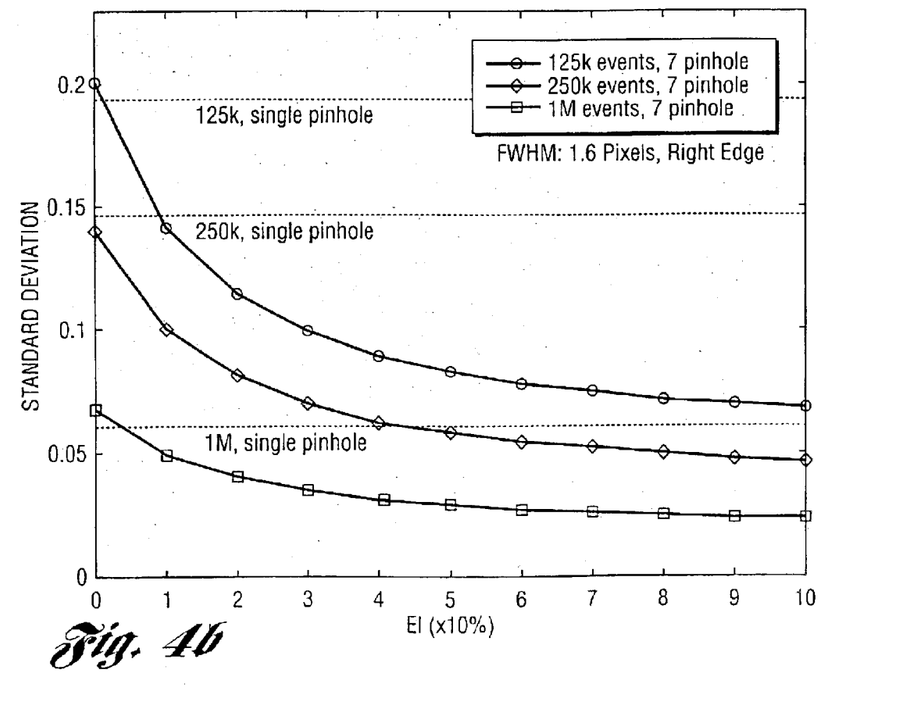

The reconstructed images, based on data sets containing 125 k events, are shown in FIG. 3. The phantom and the mean projection are also shown in FIG. 3, which shows a substantial amount of multiplexing in the data. At a given spatial resolution, the variance in the image was calculated based on the 100 realizations is shown as a function of the added extra information in FIG. 4.

It is shown that the image quality improves when extra information is added. Interestingly, most of these improvements occur in the first few steps. This is confirmed by the variance calculation. If 30% of these events are used in the reconstruction, one could get an image that is almost as good as the one achievable with a data set that contains no multiplexing at all. The angular information provided by Compton scattering is limited by factors such as detector electronic noise, Doppler broadening and finite spatial resolution. The amount of Compton scattering events one could use is also limited by the relatively low detection sensitivity of the Compton aperture. For a realistic detector design, the amount of extra information one can expect from adding the Compton scattering aperture would be very limited. For practical reasons, one may not want to use a fully optimized Compton aperture. For example, it would be advantageous if one could use existing gamma cameras as the secondary detector, while inserting an active silicon sensor as the scattering detector. The use of these less optimized Compton apertures may further reduce the extra information provided.

As described above, adding electronic collimation to a conventional mechanical collimated imaging system with multiplexing leads to a much-reduced angular ambiguity. This results in a significant reduction of noise in the reconstructed images. More interestingly, the amount of extra information (detected Compton scattering events) necessary to make a significant contribution to the image quality is relatively small, which partially compensates for the low sensitivity of the Compton aperture. Using the Compton scattering enhancement may improve the 3-D resolution of the detector with limited view angle. This is important for imaging applications, in which one would get as much information as possible from limited angles.

Some unique benefits offered by the method and system of the present invention may be summarized below:

This invention offers a better trade-off between the detection sensitivity and spatial resolution. For some applications, it has the potential of outperforming those commercial Gamma cameras currently used in many hospitals. For example, in applications such as scintimammography, its superior imaging performance may lead to an improved accuracy in early detection of tumors in breast tissue.

A valuable improvement in image quality may be achievable by adding only a small amount of information through the Compton scattering enhancement. Therefore, another commercially attractive approach may be that instead of designing an all-new imager, existing Gamma cameras can be "upgraded" to offer better performance. This is done by replacing the parallel hole or pinhole collimator with a multiple pinhole collimator and inserting a Compton scattering detector between the Anger camera and the collimator.

This invention may also be beneficial in designing an imaging system for nuclear environments, in which it is necessary to be able to image gamma ray sources with higher energies, up to a few MeV. In this energy range, Compton scattering in detectors has a reasonably high probability and mechanical collimation becomes less effective due to gamma ray penetration. Therefore, an imaging system with a combined electronic and mechanical collimation may produce a superior imaging capability.

The method and system can improve performance over either a mechanically collimated system or a straight Compton camera—especially at lower energies, which have traditionally been a problem for Compton imaging.

The method and system reduce the amount of computation associated with Compton camera reconstruction (and improves image quality at the same time).

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for generating an image of the radiation density of a source of photons located in an object, the method comprising:

positioning first and second detectors in a spaced-apart relationship in a detector space;

mechanically collimating photon emissions from the object to allow some mechanically-collimated photon emissions to enter the detector space while rejecting other photon emission from entering the detector space;

utilizing the detectors to detect Computon scattering events between the dectors;

utilizing the first and second detectors to detect non-Compton scattering events which interact with either the first detector or the second detector, but not with both detectors; and reconstructing an image from data containing detected Compton scattering events and detected non-Compton scattering events wherein the detected Compton scattering events provide angular information used in the step of reconstructing to improve image quality and wherein the angular information is based on a surface defined by energy deposited in the first detector and interaction positions in both of the detectors.

2. The method as claimed in claim 1, wherein the step of mechanically collimating includes the step of sampling the object at several view angles substantially simultaneously.

3. A system for generating an image of the radiation density of a source of photons located in an object, the system comprising:

a mechanical collimator to mechanically collimate photon emissions from the object to allow some mechanically-collimated photon emissions to enter a detector space while rejecting other photon emissions from entering the detector space;

first and second detectors spaced-apart in the detector space for detecting Compton scattering events between the detectors and non-Compton scattering events which interact with either the first or the second detector only and not with both detectors; and a processor for reconstructing an image using data containing detected Compton scattering events and detected non-Compton scattering events wherein the detected Compton scattering events provide angular information based on a surface defined by energy deposited in the first detector and interaction positions in both of the detectors to improve image quality.

4. The system as claimed in claim 3, wherein the detectors include a scintillation detector and a scattering detector provided between the mechanical collimator and the scintillation detector.

5. The system as claimed in claim 4, wherein the scintillation detector is position-sensitive.

6. The system as claimed in claim 4, wherein the scattering detector is a detector array.

7. The system as claimed in claim 6, wherein the detector array is a silicon pad detector array.

8. The system as claimed in claim 4, wherein the mechanical collimator includes a multiple-pinhole collimator and wherein a different probability is assigned for each pinhole by the angular information.

9. The system as claimed in claim 8, wherein the probability assigned each pinhole is based upon position recorded in the scintillation detector in the case of non-Compton scattering events.

10. The system as claimed in claim 8, wherein the probability assigned each pinhole is based upon positions and energies recorded in the scintillation and scattering detectors in the case of Compton scattering events.

11. The system as claimed in claim 3, wherein the mechanical collimator includes a multiple-pinhole collimator and wherein the object is sampled at several view angles substantially simultaneously.

12. The system as claimed in claim 3, wherein the mechanical collimator is spatially or temporally modulated.

13. The system as claimed in claim 12, wherein the mechanical collimator has a favorable cross-correlation pattern with the Compton detector.

14. The system as claimed in claim 3, wherein the detectors include an Anger camera.

15. The system as claimed in claim 3, wherein the detectors include a scattering detector.

16. The system as claimed in claim 3, wherein the photon emissions are gamma emissions.

* * * * *

UNITED STATES PATENT AND TRADEMARK OFFICE
CERTIFICATE OF CORRECTION

PATENT NO. : 6,881,959 B2
DATED : April 19, 2005
INVENTOR(S) : Ling Jian Meng et al.

It is certified that error appears in the above-identified patent and that said Letters Patent is hereby corrected as shown below:

Column 10,
Line 59, delete "emission" and insert therefor -- emissions --.
Line 60, delete "Computon" and insert therefor -- Compton --.
Line 61, delete "dectors" and insert therefor -- detectors --.

Signed and Sealed this

Twelfth Day of July, 2005

JON W. DUDAS
*Director of the United States Patent and Trademark Office*